United States Patent [19]

Buysch et al.

[11] Patent Number: 6,111,140
[45] Date of Patent: Aug. 29, 2000

[54] RU—PD HALOGEN-FREE CATALYZERS AND METHOD FOR PRODUCING CYCLOALIPHATIC AMINES

[75] Inventors: Hans-Josef Buysch; Gerhard Darsow; Otto Immel, all of Krefeld; Reinhard Langer, Tönisvorst, all of Germany

[73] Assignee: Bayer Aktiengesellschaft, Leverkusen, Germany

[21] Appl. No.: 09/269,929

[22] PCT Filed: Sep. 29, 1997

[86] PCT No.: PCT/EP97/05315

§ 371 Date: Apr. 5, 1999

§ 102(e) Date: Apr. 5, 1999

[87] PCT Pub. No.: WO98/15351

PCT Pub. Date: Apr. 16, 1998

[30] Foreign Application Priority Data

Oct. 10, 1996 [DE] Germany .................. 196 41 688

[51] Int. Cl.[7] ................................. C07C 207/00
[52] U.S. Cl. .................... 564/450; 564/462; 502/313; 502/330; 502/332; 502/333; 502/334
[58] Field of Search .................. 502/313, 330, 502/332, 333, 334; 504/450, 462

[56] References Cited

U.S. PATENT DOCUMENTS

| | | |
|---|---|---|
| 3,636,108 | 1/1972 | Brake ........................... 260/563 |
| 4,049,584 | 9/1977 | Weissel ........................ 252/470 |
| 4,161,492 | 7/1979 | Weissel ........................ 260/563 |
| 4,186,145 | 1/1980 | Weissel ........................ 260/563 |
| 4,429,155 | 1/1984 | Göetz et al. .................. 564/402 |
| 4,496,666 | 1/1985 | Pesa et al. .................... 518/706 |
| 4,943,549 | 7/1990 | Immel et al. ................. 502/304 |
| 4,952,549 | 8/1990 | Immel et al. ................. 502/330 |
| 4,960,941 | 10/1990 | Vedage et al. ............... 564/450 |
| 5,023,226 | 6/1991 | Immel et al. ................. 502/313 |
| 5,245,082 | 9/1993 | Immel et al. ................. 564/451 |
| 5,322,965 | 6/1994 | Immel et al. ................. 564/446 |
| 5,360,934 | 11/1994 | Vedage et al. ............... 564/451 |
| 5,386,060 | 1/1995 | Immel et al. ................. 564/450 |

FOREIGN PATENT DOCUMENTS

| | | |
|---|---|---|
| 053 818 | 6/1982 | European Pat. Off. . |
| 067 058 | 12/1982 | European Pat. Off. . |
| 560 127 | 9/1993 | European Pat. Off. . |
| 1106319 | 3/1961 | Germany . |
| 6709040 | 12/1968 | Netherlands . |
| 969542 | 9/1964 | United Kingdom . |

OTHER PUBLICATIONS

Journal of Org. Chem., vol. 29, Sep.–Dec. 1964, pp. 3082–3084.
Chem. Abstracts, vol. 120, Abstract No. 54237x, Sep. 1993.
Chem. Abstracts, vol. 71, Abstract No. 60833e, Jan. 1968.

*Primary Examiner*—Samuel Barts
*Attorney, Agent, or Firm*—Joseph C. Gil; Diderico van Eyl

[57] ABSTRACT

Catalysts containing ruthenium and palladium for the hydrogenation of aromatic amines to cycloaliphatic amines. Methods for making and using the catalysts.

20 Claims, No Drawings

RU—PD HALOGEN-FREE CATALYZERS AND METHOD FOR PRODUCING CYCLOALIPHATIC AMINES

This application is a 371 of PCT/EP97/05315 filed Sep. 29, 1997.

BACKGROUND OF THE INVENTION

The present invention relates to catalysts comprising a support optionally doped with oxides, hydroxides and hydrated oxides of the rare earths and of manganese onto which support Ru and Pd are applied and which are treated with alkaline compounds of the alkali or alkaline earth metals and are characterized in that they contain no halogen, and a process for preparing cycloaliphatic amines by hydrogenation of the corresponding aromatic precursors in the presence of the catalysts of the invention.

It is known that aromatic amines can be hydrogenated in various ways using various catalysts. However, the development of the relevant technology teaches that it is very difficult to solve all problems which occur, for example unsatisfactory conversion, lack of selectivity caused by hydrogenolysis or condensation to form relatively high molecular weight compounds, insufficient space velocities, activity and operating life of the catalysts, sufficiently well for industrial purposes. This is shown by the many proposals which have been made on this subject over the course of time.

When Ni and Co catalysts were first employed (GB 969 542), it was soon found that supported noble metals are better catalysts (DE-AS [German Published Specification] 1 106 319). However, deaminations and condensations to form polymers, the latter particularly in the hydrogenation of polyamines, were observed, so that the reactions were restricted to low temperatures and relatively long reaction times. In addition, it was observed that $NH_3$ formed in the condensation impairs the activity of the noble metals (J. Org. Chem. 29, 3082–4 (1964), EP 324 984). On the other hand, addition of $NH_3$ makes it possible to restrict the condensation to relatively high molecular weight products. Attempts have also been made to control the high exothermicity of the hydrogenation and the associated temperature increases and by-product formation by addition of solvents (NL 6 709 040, EP 67 058) or by hydrogenation at low pressure in the gas phase (FR 1 530 477).

The addition of basic compounds such as alkalis to Ru catalysts has been found to be advantageous. This enabled the formation of polymers to be limited (U.S. Pat. No. 3,636,108, EP 53 818).

It was later found that Ru in the presence of oxides or hydroxides of Cr and Mn gives catalysts which have a greater activity and selectivity and make it possible to use smaller amounts of catalyst and carry out a hydrogenation in the absence of $NH_3$ (DE-AS [German Published Specification] 2 502 893, DE-AS [German Published Specification] 2 502 894). An additional treatment of such Ru—Cr—Mn catalysts with alkalis leads to longer operating lives and greater insensitivity of the catalysts to impurities in the starting material (EP 1 425).

Hydrogenation using Pd instead of Ru has been proposed repeatedly, but condensation occurs preferentially (dicyclohexylamine from aniline: EP 503 347) so that $NH_3$ again has to be added to avoid it (EP 53 818).

The use of Ru and Pd together on a Cr—Mn-doped or alkalized support offers an advantage if long catalyst operating lives are to be achieved. However, condensation again occurs to a considerable degree and is reduced only at very low temperatures (EP 324 983, EP 324 984). Such catalysts are, for example, suitable for the flexible preparation of mixtures of cyclohexylamine and dicyclohexylamine.

A further advance in respect of selectivity and the formation of primary amines at high conversions is achieved by using Ru on RE-Mn-doped supports (RE=rare earths). For example, cyclohexylamine is obtained in a selectivity of up to 97% at 110° C. (EP 351 661, EP 476 359).

However, all known catalysts and processes still had disadvantages in respect of conversion, selectivity to primary amines, operating life of the catalysts, necessity of using $NH_3$, etc. A serious problem in catalyst beds for the continuous trickle-phase hydrogenation is the tendency of all Ru catalysts to catalyze deaminations and hydrogenolysis of the molecules right through to methane as the temperatures increase. Thus, the hydrogenation which is itself exothermic can, for example in the case of slight deviations from a given temperature, go over, first slowly then sometimes very rapidly, into the far more strongly exothermic methanization and lead to a situation which can no longer be controlled, even as far as explosions. For this reason, very comprehensive and reliable safety precautions have to be taken when using Ru catalysts. However, this calls into question the suitability of the Ru catalysts, which are very good per se, for industrial plants.

The problems which still occur even today despite the progress which has taken place are shown by EP 560 127 filed in 1992: The Ru—Pd catalysts on alkaline supports used here can hydrogenate aromatic amines at low pressure but they allow only small throughputs of from 0.03 to 0.05 g/ml of catalyst and hour, which demands large amounts of catalyst and large reactors; $NH_3$ has to be added in large amounts and the temperatures are held in the vicinity of 160° C. Despite this, hydrogenolysis still occurs, as can be recognized by the formation of benzene and cyclohexane, while the conversion continues to be incomplete; the selectivity leaves something to be desired and the operating life of the catalyst is significantly shorter than, for example, in EP 324 983. The commencement of deactivation of the catalyst is indicated by the slowly decreasing conversion.

It was accordingly an object of the invention to provide catalysts for the hydrogenation of aromatic amines to cycloaliphatic amines, which catalysts effect complete conversion at high space velocities, have high selectivity in respect of the formation of primary cycloaliphatic amines even without addition of $NH_3$ and, in particular, no longer trigger hydrogenolysis and methanization of the substrates.

It has been found that these requirements can be met if use is made of catalysts which contain Ru and Pd and are preferably applied to alkalized supports or to RE-Mn-doped supports and are strictly halogen-free. The invention is surprising in that the influence of halide ions on the catalytically active Ru to cause hydrogenolysis and methanization as a result of the undesired over-activation described was not known. The invention is also surprising in that even small residual amounts of halide which remain in the catalyst after the preparation of such catalysts from halide-containing starting materials obviously cause this undesired property.

SUMMARY OF THE INVENTION

The present invention accordingly provides catalysts on alkalized supports containing from 0.05 to 10% by weight of Ru and Pd, based on the total weight of the catalysts, in a weight ratio of from 1:30 to 30:1, which are characterized in that they contain no halogen.

The invention further provides a process for the hydrogenation of aromatic amines to cycloaliphatic amines without the above problems.

DETAILED DESCRIPTION OF THE INVENTION

The process of the invention therefore provides for the use of halogen-free catalysts containing from 0.05 to 10% by weight of Ru and Pd, based on the total weight of the catalyst, in a weight ratio of Ru to Pd of from 1:10 to 10:1 on alkalized supports for the hydrogenation of aromatic amines to cycloaliphatic amines.

The alkalized catalyst supports are preferably doped with compounds of the rare earth metals (REs) and of manganese if oxide compounds of the REs and/or of Mn do not themselves constitute the support. This doping means a content of from 0.05 to 8% by weight, preferably from 0.2 to 5% by weight, calculated as metal for the sum of RE and Mn and based on the total weight of the catalyst, with the weight ratio of RE to Mn being from 5:1 to 1:5, preferably from 10:9 to 1:2.

For the purposes of the invention, halogen-free means that the catalysts contain no halogen, i.e. no F, Cl, Br and particularly no Cl, and are therefore advantageously prepared from starting materials which do not contain halogen. The sum of the halogen contents of all starting materials for preparing the catalyst is therefore less than 1.5% by weight, preferably <0.8% by weight, particularly preferably <0.3% by weight, very particularly preferably <0.1% by weight, based on the total amount thereof. This means that the catalytically active sites, in particular the RE-Mn coating and the noble metals, remain halogen-free. On the other hand, halogen which is fixed in the interior of a support substance and is immobile even under preparation and reaction conditions does not interfere.

Starting compounds for preparing the catalysts of the invention are therefore halogen-free compounds of Ru and Pd and, if present, RE and Mn. Examples which may be mentioned are nitrates, acetates and organic complexes with acetylacetone or amino acids.

Supports for the catalysts of the invention are clay minerals, $Al_2O_3$ in its various modifications ($\alpha$, $\kappa$, $\eta$, $\gamma$), preferably the $\gamma$ modification, also supports which are otherwise customary for noble metals, e.g. $TiO_2$, kieselguhr, silica gel, $BaCO_3$, $CaCO_3$, ZnO, MgO, pumice, $ZrO_2$ and naturally also the oxides or hydrated oxides of Mn and REs, preferably $TiO_2$, $BaCO_3$, MgO, particularly preferably $Al_2O_3$ in the $\gamma$ modification, Mn and REs. In the abovementioned way, Mn and REs are predominantly used as dopants for other supports.

For the purposes of the present invention, REs are the elements of transition group III of the Periodic Table (Mendeleev), namely scandium, yttrium, lanthanum and lanthanides. As RE, it is possible to use either one of the elements mentioned or a mixture of a plurality of them. This is particularly important because even crude mixtures of REs which are industrially available and are initially enriched in only one or two of the REs can be used. Preference is given to using one or more elements selected from the group consisting of yttrium, lanthanum, cerium, praseodymium, neodymium and dysprosium. Particular preference is given to using cerium and/or lanthanum. Very particular preference is given to using cerium, if desired in a cerium-enriched mixture. For application to the support, the REs and manganese are present in the form of the compounds, preferably in oxidic form.

The catalysts of the invention must contain basic additives. Basic additives which can be used are the oxides, hydroxides or carbonates of the alkali metals or alkaline earth metals, preferably NaOH and KOH. Here, the basic additives can be applied to the catalyst support before or after coating with metal.

The catalysts can be prepared, preferably on RE-Mn-free supports, by applying the noble metals in the form of suitable salts and the alkaline compounds separately to one of the supports mentioned in the form of extrudates, pellets, spheres or granules having a diameter of from 1 to 10 mm and drying after each application.

Drying is carried out in a known manner, e.g. at from 30 to 200° C. under reduced pressure or atmospheric pressure (from 1 to 1000 mbar), for instance in a water pump vacuum. Preference is given to using aqueous solutions in the preparation. However, it is also possible to use, or make concomitant use of, organic solvents such as alcohols, lower carboxylic acids, lower nitriles, amides and lactones, as long as the starting materials are soluble therein. The alkaline compounds are applied in amounts of from 0.1 to 15% by weight, preferably from 0.2 to 10% by weight, particularly preferably from 0.3 to 8% by weight, and the noble metals are applied in amounts of from 0.05 to 10% by weight, preferably from 0.1 to 5% by weight, where these contents are based on the total weight of the catalyst.

Ru and Pd are present in a weight ratio of from 1:30 to 30:1, preferably from 1:10 to 10:1, particularly preferably from 2:8 to 8:2. Up to 20% by weight of the amount of Ru and Pd can be replaced by other noble metals such as Pt, Ir, Rh, Ag and Au.

If a support is first doped with RE and Mn, this can be carried out, for example, by impregnating or spraying the support with solutions of suitable salts of these elements. The salts of RE and Mn are converted into oxidic compounds adhering to the support by heating at temperatures from about 200 to 450° C. However, the application of the compounds of RE and Mn can also be carried out by coprecipitation of RE and Mn hydroxide mixtures on the impregnated support using alkaline compounds of alkali metals or alkaline earth metals or $NH_3$ and, if desired, subsequent washing out of soluble components using water. The support which has been pretreated in this way is dried and then preferably heated at from 200 to 450° C., preferably from 250 to 430° C., for from 1 to 120 hours; the temperature can also be increased gradually within the range indicated. Use is made, for example, of the acetates, nitrates or sulfates of REs and Mn.

The support which has been prepared in this way is subsequently impregnated or sprayed with solutions of the noble metals Ru and Pd. This is carried out using, for example, the acetates and nitrates. This application of the noble metals can be carried out in one step using dissolved mixtures of the salts or in succession using the solutions of the individual compounds. The catalyst should be dried after each application.

However, the support impregnated with noble metal can also be treated with a solution of the abovementioned alkali metal compound or alkaline earth metal compound before drying, with the noble metal being precipitated as oxide or hydroxide. This can be followed by washing out soluble components and finally drying again. Before use, this catalyst is advantageously activated with hydrogen at from 80 to 350° in the reactor.

The catalyst can, however, also be prepared by first impregnating the RE-Mn-doped support with a solution of the basic compounds mentioned, drying it and then applying to it the solutions of the noble metal salts, with the oxides and hydroxides of the noble metals being precipitated. After washing with water to remove soluble components and drying, the catalyst can be activated and used for the hydrogenation.

Treatment with alkali metal compounds or alkaline earth metal compounds before application of the noble metal compounds is not absolutely necessary. However, it is imperative that the catalyst be treated with alkali at some point in its preparation, preferably before the application of the noble metals, particularly preferably thereafter.

Suitable starting materials for the process of the invention are aromatic amines as are comprehensively described in, for example, DE-AS [German Published Specification] 2 502 894 and U.S. Pat. No. 3,636,108. Preference is given to aniline, $C_1$–$C_6$-alkylanilines, N-$C_1$–$C_6$-alkylanilines, N,N-bis-($C_1$–$C_6$-alky)-anilines, diaminobenzene, $C_1$–$C_6$-alkyated diaminobenzenes, aminonaphthalenes and $C_1$–$C_3$-alkylated aminonaphthalenes, diaminonaphthalenes, diamino-dipheny-$C_1$–$C_6$-alkanes, $C_1$–$C_{12}$-alkyl-diamino-diphenyl-$C_1$–$C_6$-alkanes and bisaminophenyl-disopropylbenzenesor a mixture of a plurality thereof.

Examples which may be mentioned are aniline, N-methylaniline, N-ethylaniline, N,N-dimethylaniline, N,N-diethylaniline, N-ethyl-toluidines, N-cyclohexylaniline, N-cyclohexylideneaniline, o-, m-, p-toluidine, 1,2,4-, 1,2,3-, 1,3,4- and 1,3,5-xylidine, o-, m-, p-phenylenediamine, 2,4-, 2,6- and 2,3-diaminotoluene, diphenylamine, bis-(4-aminophenyl)-methane, 2,4-bisaminophenyl-methane, bis-(2-aminophenyl)-methane, the mixtures of bisaminophenyl-methanes and their oligomers obtainable in the condensation of aniline with formaldehyde, bis-(4-aminodiphenyl)-propane,α,α'-bis-(4-aminodiphenyl)-m- and -p-diisopropylbenzene, 2,2',6,6'-tetramethyl-4,4'-diaminodiphenylmethane, 2,2',6,6'-tetraethyl-4,4'-diaminodiphenylmethane, 1- and 2-aminonaphthalene, 1,4-, 1,5-, 2,5-, 2,6- and 2,7-diaminonaphthalene. Preference is given to N-cyclohexylaniline, N-cyclohexylideneaniline, o-, m-, p-phenylenediamine, 2,3-diaminotoluene, diphenylamine, bis-(4-aminophenyl)-methane, 2,4-bisaminophenyl-methane, bis-(2-aminophenyl)-methane aniline, 2,4- and 2,6-diaminotoluene and the mixtures of bisaminophenyl-methanes and their oligomers obtainable in the condensation of aniline with formaldehyde.

The process of the invention is carried out at pressures of 10 and 600 bar, preferably from 50 to 500 bar, particularly preferably from 70 to 400 bar, and temperatures of from 100 to 350° C., preferably from 150 to 300° C. It can be carried out batchwise in autoclaves, preferably continuously in the downflow mode. The space velocity over the catalyst is advantageously from 0.1 to 3 g/ml.h, preferably from 0.2 to 2.5 g/ml.h, particularly preferably from 0.3 to 2.0 g/ml.h. The amount of hydrogen can be from 2 times to 100 times, preferably from 10 times to 40 times, that necessary for the hydrogenation.

The addition of $NH_3$ during the reaction is not necessary, but it need not be strictly ruled out either. Should a proportion of $NH_3$ in the reaction mixture be advantageous for particular reasons, it can be introduced without difficulties.

The invention is further described in the following illustrative examples. All references to parts and percentages are by weight unless otherwise indicated.

EXAMPLE 1

(Preparation of a Catalyst Support)

5.0 1 (4.01 kg) of a commercial γ-$Al_2O_3$ having a BET surface area of 310 $m^2$/g as spheres having a diameter of from 2 to 5 mm (SPH 501 from Rhone-Poulenc) were stirred with 1.89 l of an aqueous solution of 248 g of $Ce(NO_3)_3$.$6H_2O$ and 365.5 g of $Mn(NO_3)_2$.$4H_2O$ until the solution had been completely absorbed and were then dried under reduced pressure at 100° C. 1.75 l of an aqueous solution of 204 g of NaOH were then applied in the same way, the support was allowed to stand for 24 hours, washed with water until free of nitrate, dried at 100° C. under reduced pressure and finally calcined for 4 hours at 400° C.

EXAMPLE 2

(Preparation of a Catalyst Support)

Example 1 was repeated but without the subsequent treatment with NaOH, and at the end of the preparation the support was calcined first for 3 hours at 300° C. and, as in Example 1, for 4 hours at 400° C.

EXAMPLE 3 to 13

(General)

The catalysts were tested in the following way: a stainless steel pressure tube having a length of 60 cm and a diameter of 1.8 cm was charged with from 25 to 50 ml of catalyst, the free volume was filled with wire mesh rings of stainless steel and the catalyst was treated with hydrogen for about 24 hours at 180° C. and 270–280 bar. By means of a pump, aniline was then metered in in such an amount that the space velocity over the catalyst was 1 g of aniline/ml of catalyst×h and the hydrogenation was carried out at a pressure of 270–280 bar and 22 l of $H_2$/ml of catalyst×h. The temperature was varied and after each adjustment kept constant for from 30 to 120 hours. The reaction mixture was analyzed by gas chromatography for the following compounds (% by weight):

| | |
|---|---|
| Benzene(BE) Aniline(AN) Cyclohexane(CAN) Cyclohexanol(COL) Cyclohexylamine(CHA) Dicyclohexylamine(DCHA) | Determined in the liquid and gas phase. |
| Diphenylamine(DPA) N-Cyclohexylamine(NCHAN) Other by-products(BP) | These compounds were not found in any of the experiments. |
| Methane(M) Ethane(E) Propane(P) Butane(BU) Pentane(PE) Hexane(H) | Determined in the gas phase in vpm. |

EXAMPLE 3

200 g of γ-$Al_2O_3$ (SPH 501) were shaken with a solution of 10 g of NaOH in 61 g of water until all the solution had been absorbed and were then dried by means of nitrogen in a fluidized bed for 3 hours at 100° C. A solution of 3.40 g of $Pd(CH_3COO)_2$ (47% Pd) in 72.4 g of acetonitrile (analytical reagent) was then applied in the same way and the support was dried. The dry catalyst was reduced with hydrogen for 3 hours at 100° C. A solution of 2.45 g of (Ru(NO$_3$)$_3$ (32.6% Ru) in 69 g of water was then absorbed and the catalyst was again dried and reduced for 3 hours at 100° C. Finally a solution of 10 g of NaOH in 61 g of water was applied by the same method and the catalyst was dried by means of nitrogen for 3 hours at 100° C.

At 220° C., this catalyst gave an aniline conversion of 99.7%; at 300° C. the conversion was 100%.

| | The reaction product contained | | | | | | |
|---|---|---|---|---|---|---|---|
| Temp. | BE | CAN | COL | AN | BP | CHA | DCHA |
| 220° C. | 0 | 0 | 0.21 | 0.33 | 0.24 | 97.5 | 1.72 |
| 300° C. | 0 | 0.51 | 0.42 | 0 | 0.37 | 76.1 | 22.7 |

Despite a high space velocity of 1 g/ml.h, virtually complete conversion was achieved. Even at 300° C., only very small amounts of hydrogenolysis products (CAN) were found. The gas phase also contained only very small amounts of methane at 300° C.

EXAMPLE 4
(For Comparison)

100 g of the Ce—Mn-doped support from Example 1 were impregnated with 10.67 g of Na$_2$PdCl$_4$ (15% Pd) in 27 g of water, dried and reduced for 3 hours at 100° C. in a stream of hydrogen. The support was subsequently impregnated in the same way with 2.00 g of RuCl$_3$ (20% Ru) in 34 g of water, then dried and reduced. Finally, 5 g of NaOH in 30 g of water were applied and the catalyst was dried by means of N$_2$ for 3 hours at 100° C.

| | | The result of the catalyst test was | | | | | | | | |
|---|---|---|---|---|---|---|---|---|---|---|
| Temp. | BE | CAN | COL | AN | BP | CHA | DCHA | M* | E to PE* | % Losses** |
| 180° C. | 0 | 0.1 | 0.41 | 0 | 0.42 | 96.8 | 1.87 | n.d. | n.d. | 5–7 |
| 220° C. | 0 | 0.1 | 0.15 | 0 | 1.1 | 96.7 | 2.01 | n.d. | n.d. | 2–9 |
| 300° C. | 18.6 | 26.4 | 0.44 | 0 | 21.6 | 31.1 | 1.76 | 15000 | 12000 | 71–74 |

*These hydrocarbons were measured in vpm.
**Mass losses (% of aniline used) caused by hydrogenolysis to NH$_3$ and hydrocarbons.

This comparative experiment showed that at moderate temperatures a high degree of hydrogenolysis does not yet take place but there is appreciable hydrogenolysis which, owing to its exothermicity, can lead to a runaway reaction in industrial reactors.

EXAMPLE 5

180 g of the Ce—Mn-coated support prepared in Example 1 were impregnated with a solution of 4.43 g of Ru(NO)NO$_3$)$_3$ solution (16.24% Ru), 7.22 g of (Pd(NO$_3$)$_2$ hydrate (39.9% Pd) in 56.6 g of water, dried and reduced by covering with a 10% aqueous hydrazine solution for 3 hours. After washing with water until a neutral reaction was obtained, the catalyst was dried by means of air for 3 hours at 110° C. This Ru/Pd catalyst was then impregnated with a solution of 9.0 g of NaOH in 59 g of water and dried by means of nitrogen for 3 hours at 100° C.

| | The result of the test was | | | | | | |
|---|---|---|---|---|---|---|---|
| Temp. | BE | CAN | COL | AN | BP | CHA | DCHA |
| 180° C. | 0 | 0 | 0.3 | 0.3 | 0.13 | 95.3 | 3.97 |
| 220° C. | 0.03 | 0 | 0.4 | 0.1 | 0.14 | 95.3 | 4.03 |
| 300° C. | 1.27 | 0 | 0.4 | 1.4 | 3.06 | 61.2 | 34.3 |
| 180° C. | 0.02 | 0 | 0.5 | 7.1 | 0.33 | 84.3 | 7.70 |

Losses were found at none of the temperatures employed.

Despite the high activity and thus a high conversion, the catalyst caused barely any hydrogenolysis. Even after use at 300°, its performance was almost the same as before.

EXAMPLE 6

(Ru Alone, for Comparison)

180 g of the support from Example 1 were impregnated first with 11.04 g of Ru(NO$_3$)$_3$ (32.62% Ru) in 11.7 g of water and then with 9 g of NaOH in 60 g of water. After each impregnation, the catalyst was dried (3 h, 100° C., N$_2$), and after the first impregnation also reduced with H$_2$ at 100° C. for 3 hours.

| | | The result of the test was | | | | | | | | |
|---|---|---|---|---|---|---|---|---|---|---|
| Temp. | BE | CAN | COL | AN | BP | CHA | DCHA | M* | E to PE* | % Losses** |
| 180° C. | 0 | 0.06 | 0.1 | 0 | 0.4 | 97.7 | 0.2 | n.d. | n.d. | 0 |
| 220° C. | 0 | 0.08 | 0.2 | 0 | 1.8 | 97.0 | 0.6 | n.d. | n.d. | 38–43 |
| 300° C. | 0 | 0.1 | 0.2 | 0 | 49.6 | 22.2 | 0.9 | 17,000 | 9500 | >90 |

*measured as vpm in the gas phase

When the catalyst contains only Ru and no Pd, drastic hydrogenolysis sets in at >180° C. even in the absence of halogen. For this reason, the concomitant use of Pd is necessary.

n.d.=not determined

EXAMPLE 7
(For Comparison, Pd Alone, with Halogen)

100 g of the support from Example 1 were first impregnated with 13.33 g of $Na_2PdCl_4$ (15% Pd) in 24.5 g of water, dried and reduced with $H_2$ at 100° C. for 3 hours, then impregnated with 5 g of NaOH in 32.9 g of $H_2O$ and likewise dried by means of $N_2$ for 3 hours at 100° C.

In the test, it was found that the catalyst has only little activity and despite the presence of halogen, only gives a conversion of from 4 to 14%. For this reason, the concomitant use of Ru is necessary.

EXAMPLE 8
(For Comparison, Pd Alone, without Halogen)

180 g of the support from Example 1 were first impregnated with 3.75 g of $Pd(CH_3COO)_2$ (48% Pd) in 64.5 g of acetonitrile (analytical reagent), dried, reduced with $H_2$ at 100° C. for 3 hours, then impregnated with 9 g of NaOH in 58 g of $H_2O$ and dried by means of $N_2$ for 3 hours at 100° C.

In the test, a conversion of only 2–9% was found.

Examples 7 and 8 therefore indicate that Pd alone as catalytically active substance is not active enough either in the presence or absence of halogen and only the addition of Ru results in the high activity.

EXAMPLE 9

4000 g of the support from Example 1 were impregnated with 133.3 g of $Pd(CH_3COO)_2$ (48% Pd) in 1383 g of acetonitrile (analytical reagent), dried (3 h, 40° C., $N_2$) and reduced with $H_2$ at 100° C. for 3 hours. Subsequently, a solution of 49 g of $Ru(NO_3)_3$ (32.6% Ru) in 1383 g of $H_2O$ was applied in the same way, and the catalyst was dried and reduced as above. This was followed finally by impregnation with 200 g of NaOH in 1220 g of $H_2O$ and drying by means of $N_2$ for 3 hours at 100° C.

This catalyst caused appreciable hydrogenolysis only at 330° C., but this does not represent a hazard potential. The conversion at a high space velocity of 1 g/ml.h was 100° C., the selectivity for cyclohexylamine was from 98 to 99%. After use at 330°, the robust catalyst returned to its original activity and selectivity.

A pilot plant reactor comprising a pressure tube having a diameter of 30 mm and a length of 1 m was charged with 0.6 l of catalyst and the hydrogenation was carried out therein at 300 bar and 180° C. using a space velocity of 0.3 kg of aniline/l.h and a hydrogen flow of 6 standard $m^3$/h. The result corresponded to that of the above-described test (100% conversion, 98–99% selectivity for cyclohexylamine). After an operating time of 2036 hours, no sign of deactivation was observed.

EXAMPLE 10

180 g of the support prepared as described in Example 1 were impregnated with a solution of 2.21 g of $Ru(NO_3)_3$ (32.62% Ru) and 7.22 g of $Pd(NO_3)_2$hydrate (39.9% Pd) in 27.40 g of $H_2O$, dried and reduced with $H_2$ at 100° C. for 3 hours. After application of a solution of 9 g of NaOH in 60 g of water, the catalyst was again dried by means of $N_2$ for 3 hours at 100° C. The hydrogenation test at 180° C. and 220° C. gave complete conversion at a space velocity of 1 g/ml.h and selectivities of >96% for cyclohexylamine, <0.1% for benzene, 0.25% for cyclohexanol and <1% for BP. Thus, an excellent hydrogenation result without hydrogenolysis is also obtained when the catalytically active noble metals are applied together.

EXAMPLE 11

100 g of the support from Example 2, i.e with Ce—Mn doping but without alkali treatment, were impregnated with 3.33 g of $Pd(CH_3COO)_2$ (48% Pd) in 34.6 g of acetonitrile (analytical reagent), dried and reduced with $H_2$ in the usual way, then [lacuna] in the same way with 1.23 g of $Ru(NO_3)_3$ (32.62% Ru) in 34.6 g of $H_2O$, dried and reduced and finally treated with 5 g of NaOH in water and dried.

The result of the catalyst test was

| Temp. time | BE | CAN | COL | AN | BP | CHA | DCHA | M* | E to PE* | % Losses** |
|---|---|---|---|---|---|---|---|---|---|---|
| 190° C. 450 h | 0 | 0 | 0.12 | 0 | 0.1 | 98.9 | 0.8 | 0 | 0 | 0 |
| 220° C. 300 h | 0 | 0 | 0.25 | 0 | 0.01 | 99.0 | 0.7 | 4 | <1 | 0 |
| 300° C. 20 h | 0 | 0.6 | 0.2 | 0 | 1.1 | 88.5 | 9.5 | 30 | 35 | 0 |
| 330° C. 25 h | 0 | 7.1 | 0.1 | 0 | 10.2 | 66.4 | 16.1 | 1100 | 700 | ca. 2 |
| 200° C. 24 h | 0 | 0 | 0.25 | 0 | 0.2 | 98.3 | 1.2 | 0 | 0 | 0 |

| Hydrogenation test | | | | | | | | | |
|---|---|---|---|---|---|---|---|---|---|
| Temp. | BE | CAN | COL | AN | BP | CHA | DCHA | M* | E to PE* | % Losses** |
| 220° C. | 0 | 0 | 0.2 | 0 | 1.9 | 96.6 | 1.2 | n.d. | n.d. | 0 |
| 300° C. | 0 | 0.7 | 0.3 | 0 | 1.7 | 74.8 | 22.5 | 41 | 36 | <2 |
| 220° C. | 0 | 0.1 | 0.3 | 0 | 0.8 | 96.8 | 2.0 | 2 | <2 | <1 |

*measured in vpm.

According to this example, only a treatment of the catalyst was necessary for hydrogenolysis-freeoperation. The experiment again showed that the catalyst returns to the original selectivities at 200° C. after being subjected to the high thermal stress at 300° C.

EXAMPLE 12

180 g of the support from Example 1 were first impregnated with 4.43 g of Ru(NO)(NO$_3$)$_3$ solution (16.24% Ru) in 63.8 g of H$_2$O, then with 7.22 g of Pd(NO$_3$)$_2$.hydrate (39.9% Pd) in 61 g of H$_2$O and finally with 9.0 g of NaOH in 59.2 g of H$_2$O. After the first two impregnations, the catalyst was dried and reduced with H$_2$; after the last impregnation it was only dried.

| Hydrogenation test | | | | | | | | |
|---|---|---|---|---|---|---|---|---|
| Temp. | BE | CAN | COL | AN | BP | CHA | DCHA | Losses |
| 180° C. | 0 | 0 | 0.2 | 0 | 2.3 | 95.5 | 1.8 | <1 |
| 220° C. | 0 | 0 | 0.4 | 0 | 0.2 | 96.5 | 2.9 | <1 |
| 300° C. | 0 | 0 | 0.3 | 0 | 9.9 | 62.3 | 27.5 | <3 |
| 180° C. | 0 | 0 | 0.5 | 0.1 | 0.2 | 94.1 | 5.3 | <1 |

This example, too, showed that only little hydrogenolysis takes place at high temperatures, that the catalyst is robust and that it regains its high performance after thermal stressing.

EXAMPLE 13

180 g of a γ-Al$_2$O$_3$ (SPH 501 from Rhone-Poulenc) were first impregnated with 7.22 g of Pd(NO$_3$)$_2$.hydrate (39.9 % Pd) in 61 g of water, then with 4.43 g of Ru(NO)(NO$_3$)$_3$ solution (16.24% Ru) in 64 g of H$_2$O and finally with 9 g of NaOH in 59 g of H$_2$O. After each procedure, the catalyst was dried; after the first two, it was also reduced with H$_2$ at 100° C. for 3 hours.

| Hydrogenation test | | | | | | | | | |
|---|---|---|---|---|---|---|---|---|---|
| Temp. | BE | CAN | COL | AN | BP | CHA | DCHA | M* | E to PE* |
| 180° C. | 0 | 0 | 0.2 | 0.3 | 0.1 | 89.5 | 9.9 | n.d. | n.d. |
| 220° C. | 0 | <0.1 | 0.4 | 0 | 0.1 | 82.8 | 16.7 | n.d. | n.d. |
| 300° C. | 6.1 | 0 | 0.4 | 0 | 3.2 | 46.1 | 44.3 | 150 | 84 |
| 180° C. | 0 | 0 | 0.4 | 2.5 | 1.1 | 72.7 | 23.4 | n.d. | n.d. |

This catalyst without Ce—Mn doping likewise displayed pronounced resistance to hydrogenolysis. The selectivity for CHA was not as high as with Ce—Mn doping, but here, too, the catalyst achieved almost its old activity after thermal stressing.

Although the invention has been described in detail in the foregoing for the purpose of illustration, it is to be understood that such detail is solely for that purpose and that variations can be made therein by those skilled in the art without departing from the spirit and scope of the invention.

What is claimed is:

1. Catalysts on an alkalized support containing from 0.05 to 10% by weight of Ru and Pd, based on the total weight of the respective catalysts, in a weight ratio of Ru:Pd of from 1:30 to 30:1, wherein they contain no halogen.

2. Catalysts according to claim 1, wherein the alkalized support is doped with compounds of the rare earth metals and manganese, wherein the total amount of rare earth metals and manganese, calculated as metals and based on the total weight of the catalysts, is from 0.05 to 8% by weight, and the weight ratio of rare earth metals to manganese is from 5:1 to 1:5.

3. Catalysts according to claim 1, wherein the alkalized support means a support that has a content of a member selected from the group consisting of oxides, hydroxides, carbonates of alkali metals, carbonates of alkaline earth metals and mixtures of a plurality thereof, in an amount of from 0.1 to 15% by weight.

4. Catalysts according to claim 1, wherein the amount of Ru and Pd is from 0.1 to 5% by weight.

5. Catalysts according to claim 1, wherein the freedom from halogens is achieved by using starting materials, whose sum of halogen contents is from 0 to below 1.5% by weight for the preparation of the catalysts.

6. Catalysts according to claim 2, wherein the total amount of rare earth metals and manganese, calculated as metals and based on the total weight of the catalysts, is from 0.2 to 5% by weight, and the weight ratio of rare earth metals to manganese is from 10:9 to 1:2.

7. Catalysts according to claim 3, wherein the alkalized support comprises a member selected from the group consisting of NaOH, KOH and mixtures of NaOH and KOH in an amount ranging from 0.2 to 10% by weight.

8. Catalysts according to claim 7, wherein the alkalized support comprises a member in an amount ranging from 0.3 to 8% by weight.

9. Catalysts according to claim 5, wherein the freedom from halogens is achieved by making the catalyst component from starting materials, whose sum of halogen contents is from 0 to below 0.8% by weight, for the preparation of the catalysts.

10. Catalysts according to claim 9, wherein the freedom from halogens is achieved by using starting materials, for the preparation of the catalysts, whose sum of halogen contents is from 0 to below 0.3% by weight.

11. A process for preparing cycloaliphatic amines comprising the step of hydrogenating aromatic amines, wherein the hydrogenation is carried out over catalysts according to claim 1.

12. Process according to claim 11, wherein the process is carried out at pressures of from 10 to 600 bar, and temperatures of from 100 to 350° C.

13. Process according to claim 11, wherein the aromatic amines used comprise a member selected from the group consisting of aniline, $C_1$–$C_6$-alkylanilines, N-$C_1$–$C_6$-alkylanilines, N,N-bis-($C_1$–$C_6$-alkyl)-anilines, diaminobenzene, $C_1$–$C_6$-alkyl-diaminobenzenes, aminonaphthalenes, $C_1$–$C_3$-alkyl-aminonaphthalenes, diaminonaphthalenes, diaminodiphenyl-$C_1$–$C_6$-alkanes, $C_1$–$C_{12}$-alkyl-diamino-diphenyl-$C_1$–$C_6$-alkanes, bisaminophenyl-diisopropylbenzenes and mixtures of a plurality thereof.

14. Process according to claim 11, wherein the amount of $H_2$ is from 2 to 100 times the amount necessary for the hydrogenation.

15. Process according to claim 11, wherein the space velocity over the catalyst is from 0.1 to 3 g of aromatic amine per ml of catalyst per hour.

16. The process of claim 11, wherein the process is carried out at pressures of from 50 to 500 bar and a temperature of from 100 to 350° C.

17. The process of claim 16, wherein the process is carried out at a pressure from 70 to 400 bar.

18. The process of claim 14, wherein the amount of $H_2$ is from 10 to 40 times the amount necessary for the hydrogenation.

19. The process of claim 15, wherein the space velocity over the catalyst is from 0.2 to 2.5 g/ml.h.

20. The process of claim 19, wherein the space velocity over the catalyst is from 0.3 to 2 g/ml.h.

* * * * *